United States Patent
Kahn et al.

(10) Patent No.: US 7,987,070 B2
(45) Date of Patent: Jul. 26, 2011

(54) EYEWEAR HAVING HUMAN ACTIVITY MONITORING DEVICE

(75) Inventors: Philippe Kahn, Aptos, CA (US); Arthur Kinsolving, Santa Cruz, CA (US); Mark Andrew Christensen, Santa Cruz, CA (US); Brian Y. Lee, Aptos, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 578 days.

(21) Appl. No.: 12/108,486

(22) Filed: Apr. 23, 2008

(65) Prior Publication Data
US 2009/0234614 A1    Sep. 17, 2009

Related U.S. Application Data

(60) Provisional application No. 60/926,027, filed on Apr. 23, 2007.

(51) Int. Cl.
G01C 22/00 (2006.01)
G02C 5/00 (2006.01)
G01P 21/00 (2006.01)

(52) U.S. Cl. ............ 702/160; 351/41; 73/1.38

(58) Field of Classification Search .......... 702/160, 702/1, 33, 41, 81, 84–85, 92, 94–99, 127, 702/130–131, 133, 136, 138–142, 149–154, 702/158, 182–183, 188–189; 351/41, 83, 351/111, 158; 340/384.1, 540, 573.1, 669–670, 340/686.1, 815.4, 815.58, 870.01–870.02, 340/870.04–870.05; 73/1.37–1.38, 1.75–1.77, 73/1.79, 488, 490, 492, 495, 510–511, 514.01, 73/530

See application file for complete search history.

(56) References Cited

U.S. PATENT DOCUMENTS

| 6,522,266 | B1 | 2/2003 | Soehren et al. |
| 7,185,983 | B2 | 3/2007 | Nelson et al. |
| 7,753,861 | B1 * | 7/2010 | Kahn et al. ............... 600/595 |
| 2005/0033200 | A1 | 2/2005 | Soehren et al. |
| 2005/0248718 | A1 | 11/2005 | Howell et al. |

OTHER PUBLICATIONS

Sabelman et al., Accelerometric Activity Identification for Remote Assessment of Quality of Movement, Sep. 1-5, 2004, Proceedings of the 26th Annual International Conference of the IEEE EMBS, pp. 4781-4784.*

Avizzano, CarloAlberto, et al., "Head Tracking Based on Accelerometer Sensors", 6 pages, PERCRO, Scuola Superiore S. Anna, Pisa Italy, 2004.

Vadas, Kristin, et al., "Reading on the Go: An Evaluation of Three Mobile Display Technologies", 16 pages, College of Computing, Department of Industrial and Systems Engineering, Georgia Institute of Technology, Atlanta, GA 30332, 2006.

(Continued)

*Primary Examiner* — Michael P Nghiem
*Assistant Examiner* — Toan M Le
(74) *Attorney, Agent, or Firm* — Blakely, Sokoloff, Taylor & Zafman LLP; Judith A. Szepesi

(57) ABSTRACT

A method for monitoring human activity using an inertial sensor includes obtaining acceleration measurement data from an inertial sensor disposed in eyewear. The acceleration measurement data is processed to determine a user activity statistic. The user activity statistic includes at least one of a current user activity, periodic human motion count, total distance traveled, vertical distance traveled, current speed and average speed.

26 Claims, 9 Drawing Sheets

OTHER PUBLICATIONS

Margaria, Rodolfo, "Biomechanics and Energetics of Muscular Exercise", Chapter 3, pp. 105-125, Oxford: Clarendon Press 1976.
PCT/US2008/005249, International Preliminary Report on Patentability, Mailed Nov. 5, 2009, 6 pages.

PCT International Search Report and Written Opinion for International Application No. PCT/US2008/005249, mailed Sep. 29, 2008, 9 pages.

* cited by examiner

EYEWEAR HAVING HUMAN ACTIVITY MONITORING DEVICE

RELATED APPLICATIONS

This patent application claims the benefit under 35 U.S.C. §119(e) of U.S. provisional application No. 60/926,027, filed Apr. 23, 2007, which is herein incorporated by reference.

FIELD OF THE INVENTION

This invention relates to monitoring human activity, and more particularly to eyewear having a human activity monitoring device.

BACKGROUND

The development of Micro-Electro-Mechanical Systems (MEMS) technology has enabled manufacturers to produce inertial sensors (e.g., accelerometers) of sufficiently small size, cost, and power consumption to fit into portable electronic devices. Such inertial sensors can be found in a limited number of commercial electronic devices such as cellular phones, portable music players, pedometers, game controllers, and portable computers.

Step counting devices (e.g., pedometers) are used to monitor an individual's daily activity by keeping track of the number of steps that he or she takes. In general, step counting devices are clipped to a user's hip, and do not accurately count steps when placed elsewhere on a user's body.

Some step counting devices include an inertial sensor placed at specific locations on a user's body (e.g., in a user's shoe). Inertial sensors placed in a user's shoe (known as foot pods) may be used to determine a user's number of steps, speed and distance. However, conventional devices are not able to accurately determine distance and speed based on inertial sensors placed elsewhere on a user's body. Such conventional devices generally measure only a number of steps walked.

In conventional devices, the inertial sensors placed at specific locations on a user's body wirelessly transmit raw acceleration data to a mobile device (e.g., a wrist watch) having an acceleration processing unit. The acceleration processing unit counts steps based on the received acceleration data. These steps can then be displayed on the mobile device.

BRIEF DESCRIPTION OF THE DRAWINGS

The present invention is illustrated by way of example, and not by way of limitation, and can be more fully understood with reference to the following detailed description when considered in connection with the following figures.

DETAILED DESCRIPTION

Embodiments of the present invention are designed to monitor human activity using an inertial sensor. In one embodiment, accelerations are monitored from an inertial sensor disposed in eyewear. The accelerations are processed to determine one or more user activity statistics, examples of which include speed, distance, and number of steps taken. The user activity statistics may be formatted to a generic format understandable by multiple devices. The formatted user activity statistics may be wirelessly transmitted to one or more of the multiple devices.

Figure 1:
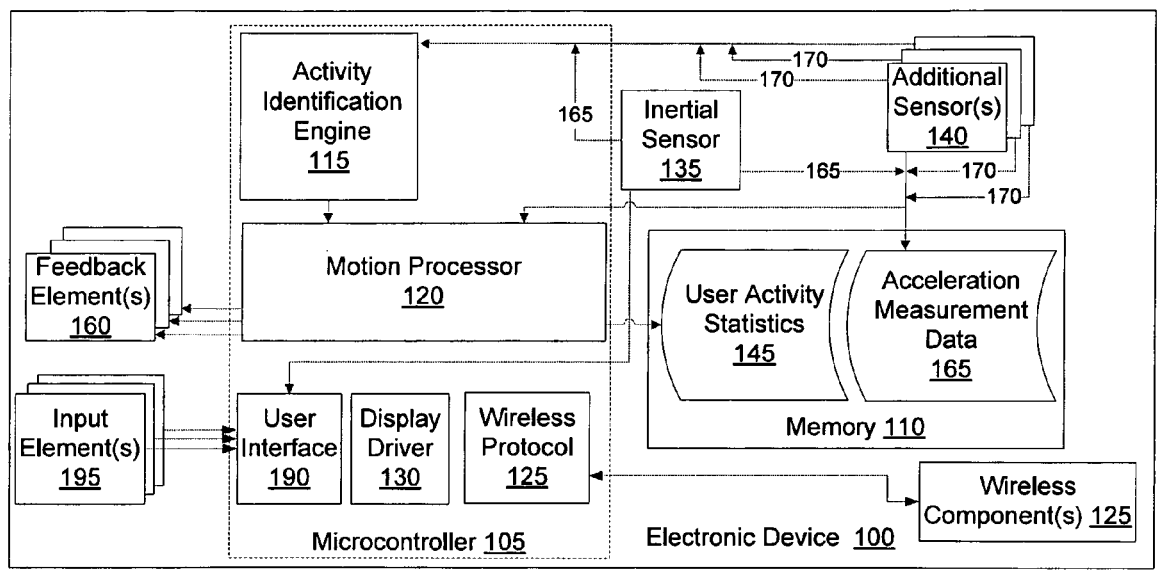
FIG. 1 is a block diagram illustrating an electronic device, in accordance with one embodiment of the present invention.

FIG. 1 is a block diagram illustrating an electronic device 100, in accordance with one embodiment of the present invention. In one embodiment, the electronic device 100 is a portable electronic device that includes one or more inertial sensors 135. The inertial sensors 135 may measure accelerations along a single axis or multiple axes, and may measure linear as well as rotational (angular) accelerations. In a further embodiment, one or more inertial sensors 135 together provide three dimensional acceleration measurement data.

The electronic device 100 may be used to identify user activities and count periodic human motions appropriate to the identified user activities. In one embodiment, electronic device 100 operates in conjunction with additional devices (e.g., a server or mobile computing device) and/or sensors to identify user activities and count periodic human motions, as shown below with reference to FIG. 2. In a further embodiment, periodic human motions may be accurately counted regardless of the placement and/or orientation of the device 100 on a user. Periodic human motions may be accurately counted whether the electronic device 100 maintains a fixed orientation or changes orientation during operation.

The electronic device 100 in the embodiment shown in FIG. 1 comprises an activity identification engine 115, a motion processor 120, an inertial sensor 135, a memory 110, a wireless protocol 125 and one or more wireless components 125. The electronic device 100 may further comprise one or more additional sensors 140 and a display driver 130.

The inertial sensor 135 may continuously generate acceleration measurement data 165 by taking measurements of acceleration. The measurements of acceleration may also be taken at a sampling rate that may be fixed or variable. In one embodiment, the inertial sensor 135 receives a timing signal from a timer (not shown) to take measurements at the sampling rate. In one embodiment, the inertial sensor 135 is coupled to the activity identification engine 115 and to the motion processor 120, and acceleration measurement data 165 is sent to the activity identification engine 115 and to the motion processor 120 for processing. The acceleration measurement data may be received by the activity identification engine 115 and the motion processor 120 at a predetermined sampling rate, which may be fixed or variable. In one embodiment, the inertial sensor 135 is coupled to the memory 110, and acceleration measurement data 165 from the inertial sensor 135 is stored in the memory 110.

In one embodiment, measurements are taken of the one or more additional sensors 140, and sent to the activity identification engine 115, the motion processor 120, and/or the memory 110. The one or more additional sensors 140 may include a heart rate sensor such as an electrocardiograph (EKG or ECG). Additional sensors 140 may also include additional inertial sensors, a pressure sensor (e.g., altimeter), a moisture sensor, a capacitance sensor, a sound sensor (e.g., microphone), a heat sensor (e.g., thermometer, thermistor, etc.), or any other sensor capable of placement in a portable device. In one embodiment, the one or more additional sensors 140 take measurements at one or more set sampling rates that may be fixed or variable. In one embodiment, the set sampling rates are the same as the sampling rate at which the acceleration measurements are taken. Alternatively, one or more of the set sampling rates may vary from the sampling rate of the acceleration measurements.

Many types of motions that are useful to keep track of have a periodic set of movements. Specific periodic human motions may be characteristic of different types of user activity. For example, to walk, an individual must lift a first leg, move it forward, plant it, then repeat the same series of motions with a second leg. In contrast, a person inline skating performs a repeated sequence of pushing, coasting and liftoff for each leg. For a particular individual, the series of walking motions will usually occur in about the same amount of time, and the series of skating motions will usually occur in about the same amount of time. The repeated set of motions can be considered a unit, and defines the motion cycle. The amount of time that it takes to complete one motion cycle defines the motion cycle's period, and the number of motion cycles that occur in a given unit of time define the motion cycle's cadence.

In one embodiment, acceleration measurement data is processed by the activity identification engine 115 to identify a user activity. The activity identification engine 115 may identify the user activity from among multiple predefined user activities. The activity identification engine 115 may identify a user activity by monitoring for different events, each event indicative of a different type of activity. Events may include positive events, which may be used to positively identify a current user activity, and negative events, which may be used to exclude user activities from consideration in determining the current user activity.

Events may be compared to predetermined motion cycle cadences and/or motion cycle periods to determine whether they occur in a proper time frame to identify a current user activity. Events that occur inside of the cadence window may identify positive events (events indicative of or reaffirming a particular user activity), while events that occur outside of the cadence window may identify negative events (events contrary to a particular user activity). Some events that occur inside of the cadence window may also identify negative events. In one embodiment, when enough events indicative of a particular user activity are detected, the activity identification engine 115 notifies the motion processor 120 that the identified activity is being performed by the user. To facilitate such a determination, a cadence window (a window of time since a last periodic human motion was counted that is looked at to detect a new periodic human motion) may be determined for a current user activity.

A cadence window may be set based on the period and/or cadence of a currently detected motion cycle (e.g., a stepping period), on set limits, and/or on other factors. In one embodiment, the cadence window is determined by measuring a length of time between periodic human motions. In one embodiment, the cadence window is a dynamic cadence window that continuously updates as a user's cadence changes during a particular activity. For example, using a dynamic cadence window, a new cadence window length may be set after each periodic human motion. In one embodiment the new cadence window length is an average of the prior cadence window lengths. For example, if the previous cadence window was 13 seconds, as averaged over 10 cycles, if the new movement cycle occurs in 10 seconds, the adjusted cadence window would be (10*13+10)/14=12.72 seconds. If no previous periodic human motions have been detected, or if fewer than a set number of periodic human motions to determine a dynamic cadence window have been detected, a default cadence window may be used. In one embodiment, a separate cadence window may be maintained for each identifiable user activity. Each identifiable user activity may have, for example, a unique default cadence window. Once a user activity is identified, those cadence windows for other (non-identified) user activities may be terminated.

In one embodiment, only acceleration measurement data is used to detect events that identify user activities. Alternatively, measurements from (and metrics associated with) one or more of the additional sensors 140 may be used to facilitate user activity identification. For example, heart rate measurements showing a heart rate greater than a threshold value may indicate that a user is exerting himself or herself, which may trigger an event for a user activity of, for example, running.

The motion processor 120 may process acceleration measurement data to detect periodic human motions. In one embodiment, a series of motion criteria are applied to the acceleration measurement data. If each of the motion criteria are satisfied, a periodic human motion may be identified, and counted. In one embodiment, a different set of motion criteria may apply for each user activity. In one embodiment, motion criteria may include positive criteria and negative criteria. In one embodiment, if any negative criteria are detected, an acceleration measurement is disqualified from being counted as a periodic human motion.

Once the activity identification engine 115 has identified a user activity, the motion processor 120 may apply a set of motion criteria specific to the identified activity to detect appropriate periodic human motions. Motion criteria may include acceleration thresholds, acceleration comparison requirements (e.g., comparisons of current acceleration measurements and previous acceleration measurements), cadence windows, etc. In one embodiment, the cadence window identifies a time frame in which positive motion criteria must be satisfied for a periodic human motion to be counted. Upper and lower motion criteria thresholds may be based on rolling averages of accelerations, statistical averages of human motions (e.g., average human running speed), maximums and minimums of human motions (e.g., fastest human running speed), etc. Motion criteria may include dynamic motion criteria that are updated continuously as current conditions change (e.g., as an inertial sensor changes orientation, as a user changes cadence, etc.) and/or static criteria that are preset, or criteria that may be changed through user input.

When an appropriate periodic human motion is detected, it may be recorded as one of the user activity statistics 145 (e.g., number of steps walked) in the memory 110. Separate user activity statistics 145 may be maintained for each type of user activity.

In one embodiment, the motion processor 120 generates user activity statistics based on measurements from the inertial sensor 135. Alternatively, one or more of the additional sensors 140 may also be used to generate user activity statistics. User activity statistics may include analyses of biomechanics of human motion. An analysis of the bio-mechanics of human motion may also be made based on the user activity statistics. Examples of user activity statistics include periodic human motion counts, distance, speed, etc.

In one embodiment, the user activity statistics are formatted by the motion processor 120 once they are generated. The user activity statistics may be formatted into one or more formats. In one embodiment, the user activity statistics are formatted to a generic format readable by multiple different computing devices. Examples of generic formats for the user activity statistics include extensible markup language (XML) and standard generalized markup language (SGML). In one embodiment, the format used for the user activity statistics is user selectable.

One type of user activity statistic is a periodic human motion count. A separate periodic human motion count may be maintained for each type of periodic human motion. For example, a separate count may be maintained for walking, running, inline skating, rowing, bicycling, and so on. A total periodic human motion count that includes all periodic human motions may also be maintained.

Other user activity statistics include heart rate, body temperature, breathing rate, distance, altitude change, and so on. These user activity statistics may be correlated to specific user activities. Therefore, a user may find out, for example, the distance run versus the distance walked during a training session, as well as average speed, average running heart rate, average walking heart rate, and so on. A user may also determine, for example, daily activity levels, weekly activity levels, etc., from the user activity statistics. This may provide a user with information useful for athletic training and health.

In one embodiment, electronic device 100 includes one or more feedback elements 160. Feedback elements 160 may be part of the electronic device 100, or may be external to the electronic device. Feedback elements 160 may provide one or more of aural feedback (e.g, a buzz, beep, tune, spoken words, etc.), visual feedback (e.g., a blinking or solid light, number display, etc.) and tactile feedback (e.g., a vibration, movement, or slight shock). Feedback may be used, for example, to notify a user to speed up or to slow down, to notify a user that a specified period of time has elapsed, etc. In one embodiment, the type of user feedback, and when to provide user feedback, is user selectable. For example, a user may select to be given a notice to slow down when the user's heart rate exceeds an upper threshold, and to speed up when the user's heart rate falls below a lower threshold. Multiple feedback conditions may be active concurrently. For example, a user may select to receive feedback if a running speed falls below a lower threshold and if a heart rate falls below a lower threshold. Thereby, a user may more accurately control workout intensity.

Figure 2:
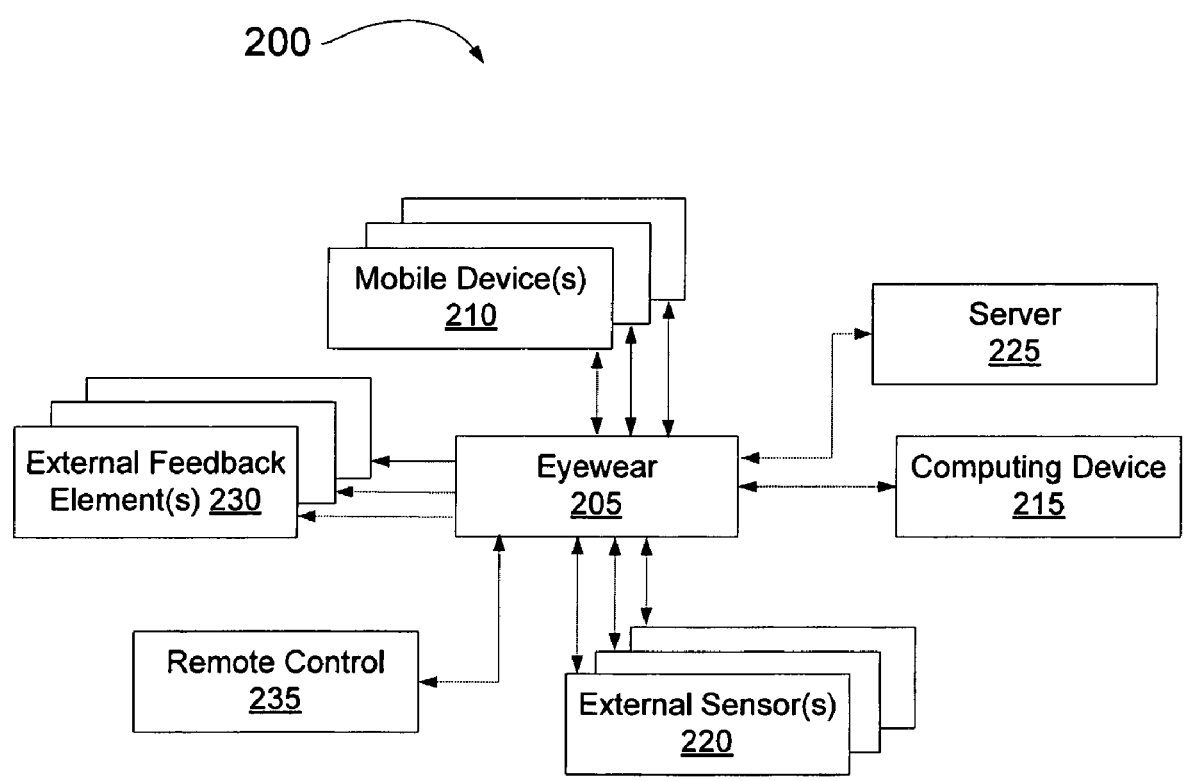
FIG. 2 is a block diagram illustrating a motion identification system, in accordance with one embodiment of the present invention.

In one embodiment, user activity statistics 145 are stored in memory 110. Alternatively, the user activity statistics may be transmitted to an additional electronic device such as a server or storage unit, as shown in FIG. 2 and described below. In one embodiment, the memory 110 stores measurement data 150, which may later be processed by the electronic device 100, or by an external device such as a server. Alternatively, measurement data 150 may not be stored, or it may be transmitted to an additional electronic device for storage.

In one embodiment, the electronic device 100 includes a wireless protocol 125 and one or more wireless components 125. The wireless protocol may be Bluetooth, Zigbee, infrared, radiofrequency (RF), personal area network (PAN), or any other wireless communication protocol. Alternatively, the electronic device 100 may include a wired protocol such as firewire, universal serial bus (USB), etc. In one embodiment, the electronic device 100 includes both a wireless protocol 125 and a wired protocol. The wireless and/or wired protocol may enable the electronic device to communicate with additional devices, such as a server, mobile device, personal computer, etc.

In one embodiment, the electronic device 100 includes a display driver 130. The display driver 130 may control a built in display (not shown) of the electronic device, or an external display (not shown) that may be connected to the electronic device 100.

In one embodiment, the electronic device 100 includes a user interface 190. The user interface 190 may communicate with the display driver 130 to control what information is displayed to a user. The user interface 190 may also control modes of operation of the electronic device, activate and/or deactivate functions, etc. The user interface 190 may be a graphical interface, an audio interface, etc.

In one embodiment, user interface 190 includes a motion command interface that receives acceleration measurement data from inertial sensor 135. The motion command interface may include a gesture recognition engine and/or a tap recognition engine. The gesture recognition engine can process received acceleration measurement data to detect a predefined user gesture, and may interpret the gesture as a command. Likewise, the tap recognition engine can process received acceleration measurement data to detect a user tap or series of taps (e.g., a tap on a particular region of electronic device 100), and may interpret the tap or taps as a command or other user input. The user input/command may determine an operating mode of electronic device 100, select display options, initiate calibration, select user activity statistics to display, etc.

In one embodiment, electronic device 100 includes one or more input elements 195. The input elements 195 can provide user input to user interface 190. The input elements 195 may include buttons, switches, dials, or other controls accessible to a user. In one embodiment, input elements 195 include a microphone. In such an embodiment, user interface 190 includes a speech recognition engine to recognize user voice commands.

In one embodiment, the activity identification engine 115, motion processor 120, display driver 130 and wireless protocol 125 are logics executed by a microcontroller 105, field programmable gate array (FPGA), application specific integrated circuit (ASIC), or other dedicated processing unit. In another embodiment, one or more of the activity identification engine 115, motion processor 120, display driver 130 and wireless protocol 125 may be logics executed by a central processing unit. Alternatively, one or more of the activity identification engine 115, motion processor 120, display driver 130 and wireless protocol 125 may include a state machine (e.g., an internal logic that knows how to perform a sequence of operations), a logic circuit (e.g., a logic that goes through a sequence of events in time, or a logic whose output changes immediately upon a changed input), or a combination of a state machine and a logic circuit.

FIG. 2 is a block diagram illustrating a motion identification system 200, in accordance with one embodiment of the present invention. The motion identification system 200 in one embodiment includes eyewear 205 wirelessly connected to one or more mobile devices 210, one or more external sensors 220, one or more external feedback elements 230, a computing device 215, a server 225, and a remote control 235. In alternative embodiments, eyewear 205 may be connected to only some of the mobile devices 210, external sensors 220, server 225, computing device 215 and remote control 235. In another embodiment, eyewear 205 is not connected to any devices or sensors. In one embodiment, eyewear 205 includes electronic device 100 of FIG. 1.

Returning to FIG. 2, distribution of the functionality between the eyewear 205 and the devices, sensors and server may vary. In one embodiment, all sensor data is processed by eyewear 205. The sensor data may be formatted by the eyewear 205 into a generic format readable by one or more of the mobile devices 210, server 225 and computing device 215. Alternatively, eyewear 205 may transmit unprocessed and/or unformatted data to one or more of the mobile devices 210, server 225, and/or computing device 215. In one embodiment, signals are sent to external feedback elements 230 to provide user feedback, for example, to indicate that user should speed up or slow down. Some or all of eyewear 205, the devices, sensors and server may include a storage device to store measurement data and/or user activity statistics.

Remote control 235 may be used to provide user input to eyewear 205. In one embodiment, a mobile device 210 may be configured to operate as a remote control for eyewear 205. For example, a user's cellular phone may operate as a remote control, thus reducing a number of items for a user to carry.

Figure 3:
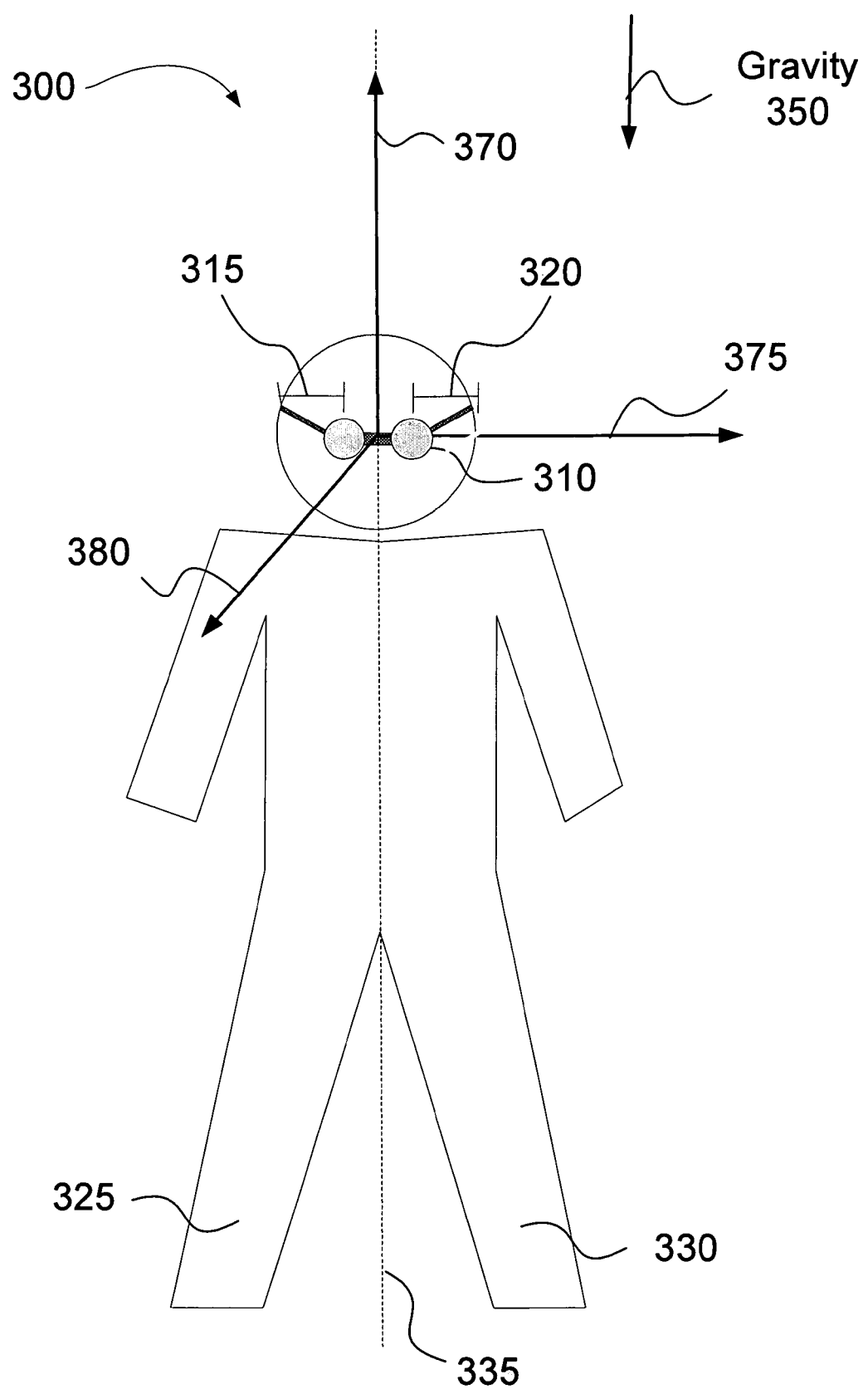
FIG. 3 illustrates a front view of a user wearing eyewear, in accordance with one embodiment of the present invention.

FIG. 3 illustrates a front view of a user 300 wearing eyewear, in accordance with one embodiment of the present invention. In one embodiment, the eyewear is eyewear 205 of FIG. 2.

Referring to FIG. 3, user 300 has an axis of symmetry 335 that divides user's 300 body into a right half 325 and a left half 330. In one embodiment, eyewear 310 is disposed on the user 300 such that a center of eyewear 310 approximately lines up with axis of symmetry 335. Therefore, eyewear 310 may be equidistant from a right side of the body 315 and from a left side of the body 320.

Placement of eyewear 310 along the line of symmetry 335 in one embodiment enables differentiation between accelerations caused by motions from the right half 325 of user's body and left half 330 of user's body. Therefore, eyewear 310 may distinguish between, for example, steps taken by a right leg and steps taken by a left leg. This may assist users in refining their running technique, or provide an indication that something may be wrong with a user's left or right leg.

In one embodiment, the eyewear 310 is disposed on user's 300 face at a fixed orientation such that a first axis 370 of the eyewear 310 is approximately aligned to gravity 350 when user 300 is standing and looking straight ahead. In one embodiment, a second axis 375 of eyewear 310 extends laterally to user 300 (Medial-Lateral Axis), and a third axis 380 of eyewear 310 extends front-to-back in relation to user's 300 body (Ventral-Dorsal Axis).

In one embodiment, the fixed orientation of the eyewear 310 enables identification of vertical movement, lateral movement, and front-to-back movement. In one embodiment, the fixed orientation of eyewear 310 further enables first axis 370 to be used for counting periodic human motions without first determining a dominant axis (e.g., an axis aligned closest to gravity). Alternatively, the dominant axis may be determined before or in conjunction with counting periodic human motions.

A dominant axis may be assigned by performing one or more of determining a motion cycle period, determining one or more rolling averages of accelerations, and determining an orientation of the eyewear based on the rolling averages of accelerations. In one embodiment, a gravitational influence is determined according to an axis of the inertial sensor having the largest absolute rolling average of accelerations. Information of the gravitational influence may then be used to assign the dominant axis (the axis most affected by gravity).

In one embodiment, the dominant axis may be used to indicate whether a user is currently wearing eyewear 310 on user's face, or whether eyewear is hanging around user's neck, or is otherwise placed on user's body. For example, the dominant axis may be compared to the first axis 370, second axis 375 and third axis 380 to determine how eyewear 310 is oriented to gravity. Moreover, if no accelerations are detected for a predetermined time period, it can be determined that the eyewear is not being worn or carried by a user. Eyewear 310 may determine user activity statistics whether eyewear 310 is being worn on user's face, or is otherwise disposed on user's person. Alternatively, eyewear 310 may determine user activity statistics only when specific eyewear placement is detected (e.g., if the eyewear is detected to be positioned on a user's face). In one embodiment, some functions are activated only when eyewear 310 is detected to have a specified orientation, and other functions are activated regardless of the orientation of eyewear 310.

Figure 4:
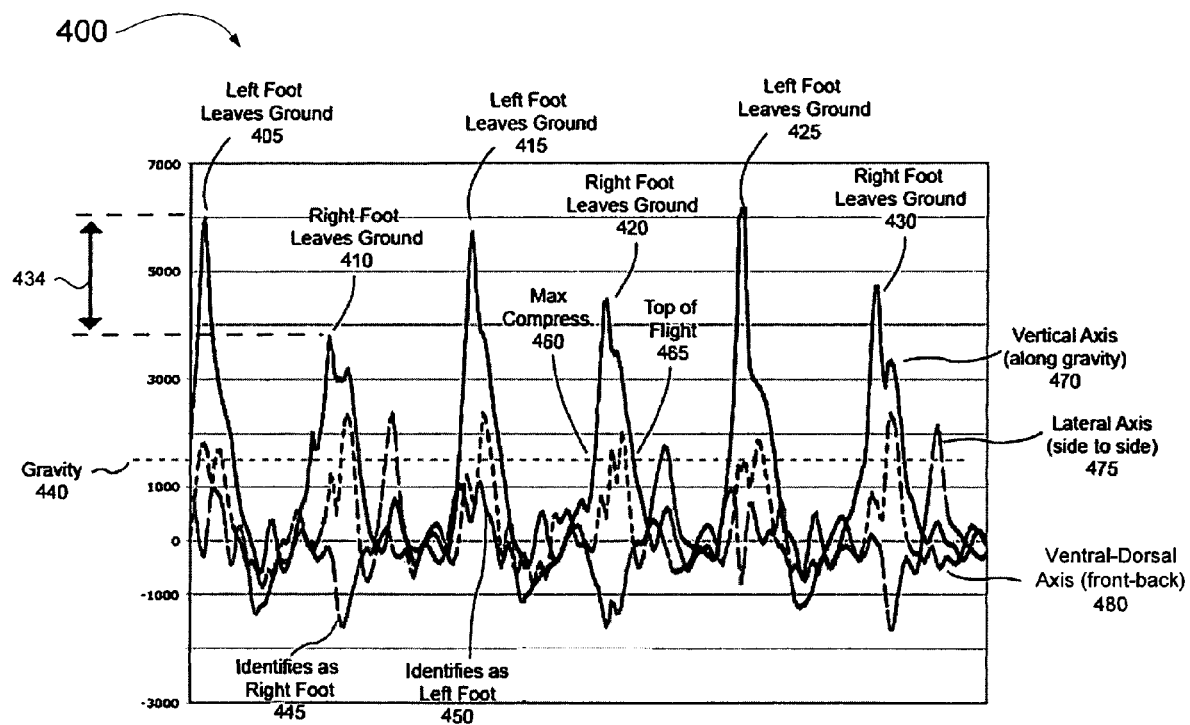
FIG. 4 illustrates an exemplary motion cycle graph that shows a user engaged in a user activity as measured by an accelerometer located in eyewear.

FIG. 4 illustrates an exemplary motion-cycle graph 400 that shows a user engaged in a user activity as measured by an accelerometer located in eyewear and aligned to user's axis of symmetry. In one embodiment, the eyewear is eyewear 310 of FIG. 3. Referring to FIG. 4, the exemplary motion-cycle graph 400 shows acceleration measurement data taken with a single tri-axis inertial sensor. The acceleration at a given period of time is represented for a vertical axis 470, a lateral axis 475, and a ventral-dorsal axis 480.

In one embodiment, the vertical axis 470 is used to identify steps. In one embodiment, gravity 440 provides a constant acceleration along the positive direction of the vertical axis 470. Accordingly, any positive acceleration along the vertical axis 470 is acceleration towards the earth, and any negative acceleration along the vertical axis 470 is acceleration away from the earth. Thus, a foot leaving the ground is indicated by a peak (spike) of acceleration along the vertical axis 470. Such peaks of acceleration are shown for the left foot 405, 415, 425 and for the right foot 410, 420, 430. In alternative embodiments, gravity may provide a permanent acceleration along the negative direction of the vertical axis 470. In such an embodiment, valleys (spikes) along the vertical axis 470 would indicate a foot leaving the ground.

Accelerations along the vertical axis 470 may be used to determine multiple different user activity statistics. In one embodiment, the vertical axis may be used to identify a magnitude of acceleration that each leg experiences. This may be useful, for example, to determine how much strain is placed on each leg during running and/or walking. In one embodiment, points at which vertical acceleration 470 crosses 465 gravity 440 (where the accelerations equal gravity) indicate that a user is in a state of free fall. In one embodiment, a shape of the peak (spike) of acceleration measurements along the vertical axis 470 indicates an elasticity of the surface being walked or run on. For example, a sharp spike can indicate a surface with relatively low elasticity (e.g., concrete), while a gradual spike can indicate a surface with relatively high elasticity (e.g., a rubber track). Surfaces with a greater elasticity absorb a greater amount of user impact, and are therefore less damaging to a user's body. Other useful data may also be determined from the vertical axis 470.

In one embodiment, lateral axis 475 is used to identify whether a step is being taken by a right foot or by a left foot. In the illustrated embodiment, any negative acceleration along the lateral axis indicates acceleration towards the right, and any positive acceleration along the lateral axis indicates acceleration towards the left. Thus, the lateral axis 475 may identify accelerations caused by the right foot 445 and accelerations caused by the left foot 450. In alternative embodiments, a positive acceleration may indicate acceleration to the right, and a negative acceleration may indicate acceleration to the left.

In one embodiment, additional specifics about a user's gait may be determined based on accelerations along the lateral axis 475, the ventral-dorsal axis 480 and/or the vertical axis 470. For example, the illustrated embodiment shows a greater acceleration along the vertical axis 470 from the left foot than from the right foot. This difference between acceleration peaks 435 along the vertical axis 470 may identify a problem with the right leg (e.g., an injury or potential injury). Acceleration measurements may identify potential or current problems even in instances in which a user fails to notice any problems. This information may be used to help prevent user injury or overtraining. Other useful information about a user's gait may also be determined, such as an amount of lateral motion accompanying each step, an amount of unnecessary vertical motion with each step, an amount of force exerted by each step, etc.

Though FIG. 4 has been described in the context of identifying steps for walking and running, the techniques described with reference to FIG. 4 may equally be used when counting other periodic human motions associated with other user activities. Examples of such additional user activities include inline skating, swimming, rowing, etc.

Figure 5:
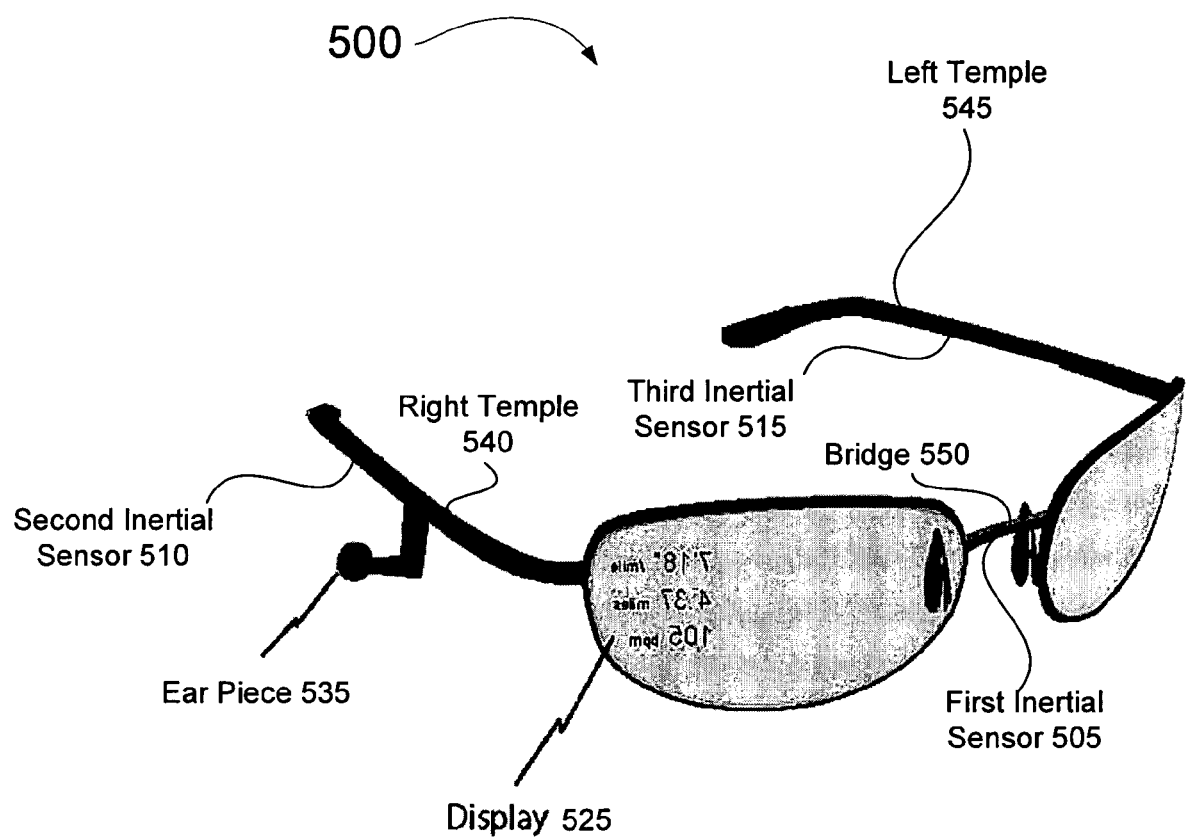
FIG. 5 illustrates a perspective view of eyewear having an inertial sensor, in accordance with one embodiment of the present invention.

FIG. 5 illustrates a perspective view of eyewear 500 having an inertial sensor, in accordance with one embodiment of the present invention. In one embodiment, the eyewear 500 includes electronic device 100 of FIG. 1. In one embodiment, eyewear 500 corresponds to eyewear 300 of FIG. 3.

In one embodiment, eyewear 500 includes a first initial sensor 505 disposed at a bridge 550 of eyewear 500. The first inertial sensor 505 may be located along an axis of symmetry of a user, as discussed with reference to FIG. 3. In other embodiments, eyewear 500 may include a second inertial sensor 510 and/or a third inertial sensor 515 instead of or in addition to first inertial sensor 505. Second inertial sensor 510 and third inertial sensor 515 in one embodiment are disposed at a right temple 540 and a left temple 545 of eyewear 500, respectively. Such placement may enable calculations of head orientation such as the direction and degree of head tilt and head twist.

Placement of inertial sensors at opposite temples may enable calculations similar to those that can be made by a single accelerometer disposed along an axis of symmetry of a user, as discussed with reference to FIGS. 3 and 4. For example, if the second inertial sensor 510 measures a greater acceleration than the third inertial sensor 515 as a foot is detected to leave the ground, then it may be determined that a right foot is taking a step. Likewise, a left step may be determined if the third inertial sensor 515 measures a greater acceleration than the second inertial sensor 510. Accelerations from the second inertial sensor 510 and third inertial sensor 515 may also be compared to analyze a user's gait. For example, if greater accelerations are detected for steps taken with a left foot than for steps taken with a right foot, it may be determined that a user has a weaker right leg.

In one embodiment, eyewear 500 includes an earpiece 535 on one or both of the right temple 540 and the left temple 545. In one embodiment, the earpiece 535 includes an audio feedback element. In another embodiment, the earpiece 535 includes a vibration feedback element. Alternatively, one or both of the right temple 540 and the left temple 545 may include the vibration feedback element and/or the aural feedback element without the ear piece 535.

In one embodiment, ear piece 535 includes an ear clip having one or more bio sensors. The bio sensors may be used to monitor one or more of heart rate, blood oxygen saturation, blood glucose, and blood pressure. In one embodiment, the bio sensors include a pulse oximeter for attachment to an earlobe. In other embodiments, bio sensors may include, a temperature sensor, a capacitance sensor, etc.

In one embodiment, eyewear 500 includes a display 525 on one or both lenses. The display may show one or more user activity statistics, such as distance run, current running speed, calories burned, etc. If the eyewear 500 includes additional sensors, such as the heart rate sensor 520 or bio sensors (not shown), or the user is wirelessly connected to external sensors, user activity statistics based on those sensors may also be shown. Display 525 may also show temporal information such as, for example, time and date, an exercise duration, a countdown timer, etc. The user activity statistics shown may be user selectable.

Figure 6:
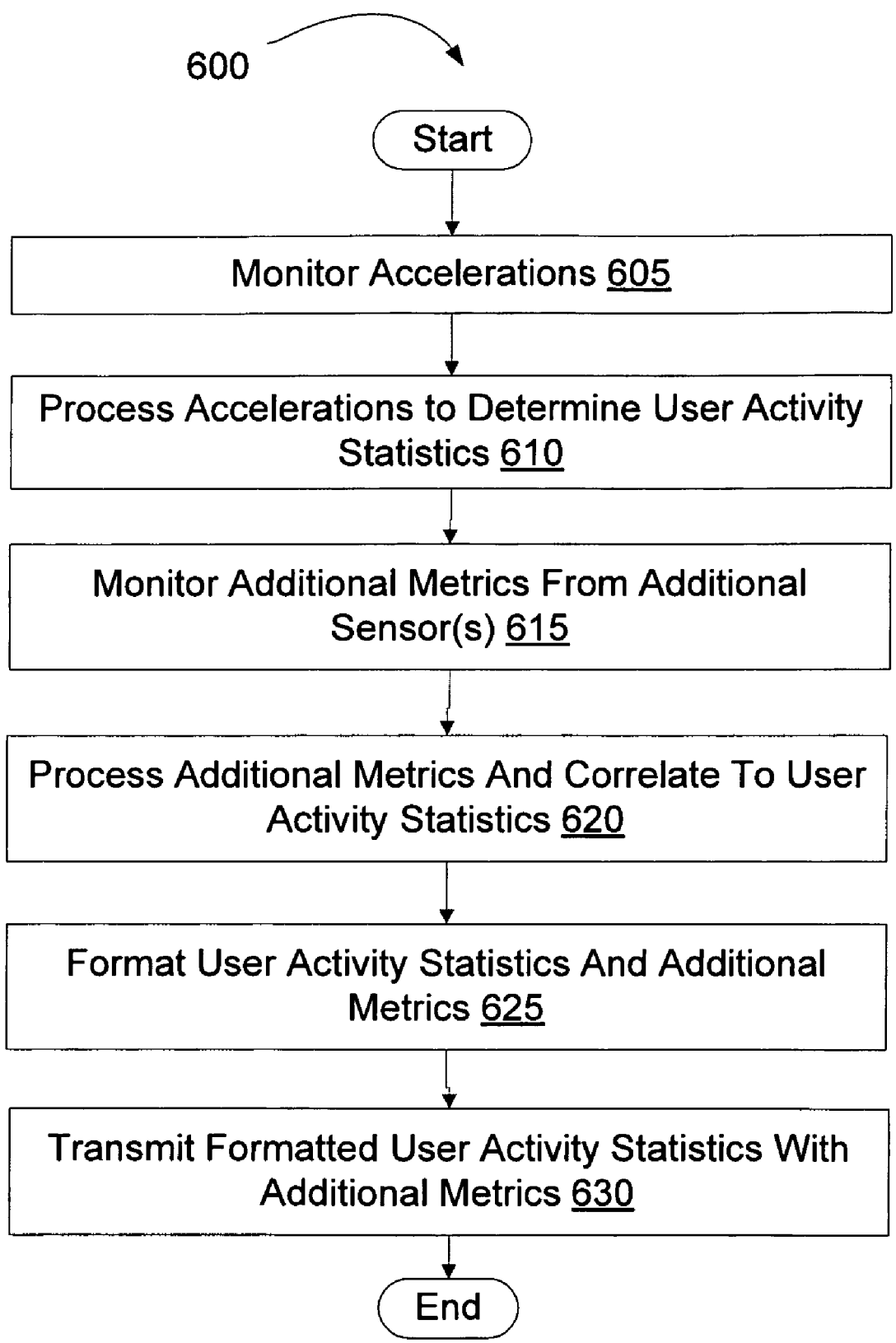
FIG. 6 illustrates a flow diagram for a method of monitoring human activity using an inertial sensor, in accordance with one embodiment of the present invention.

FIG. 6 illustrates a flow diagram for a method 600 of monitoring human activity using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 600 is performed by the electronic device 100 of FIG. 1. In one embodiment, method 600 is performed by the motion identification system 200 of FIG. 2.

Referring to FIG. 6, method 600 begins with obtaining acceleration measurement data (block 605). Acceleration measurement data may be obtained from an inertial sensor, or other acceleration monitoring device. At block 610, the accelerations are processed to determine user activity statistics. In one embodiment, the accelerations are processed by a motion processor.

At block 615, metrics are monitored from one or more additional sensors. Examples of additional sensors include a heat sensor, a pressure sensor, a heart rate sensor, etc. Examples of metrics include heart rate, body temperature, altitude, etc.

At block 620, the metrics are processed and correlated to the user activity statistics. Such processing and correlation may be performed by, for example, motion processor 120 of FIG. 1. At block 625, the user activity statistics and the metrics are formatted. In one embodiment, the user activity statistics are formatted into a generic format understandable by multiple different computing devices. Examples of a generic format include XML and SGML. In one embodiment, the "generic" format may be selected by the user. The user may select the format from a remote control, from a control mounted on the eyewear, or from a computing device, server or mobile device connected to the eyewear. In one embodiment, the generic format includes formats such as spreadsheet formats, comma-delimited formats, human readable formats, etc.

At block 630, the formatted user activity statistics are transmitted along with the additional metrics for further processing or storage. In one embodiment, the formatted user activity statistics and additional metrics are transmitted to a mobile device such as a mobile phone, personal digital assistant (PDA), laptop computer, wrist watch, etc. Alternatively, the formatted user activity statistics may be transmitted to a server and/or a computing device such as a personal computer.

Figure 7:
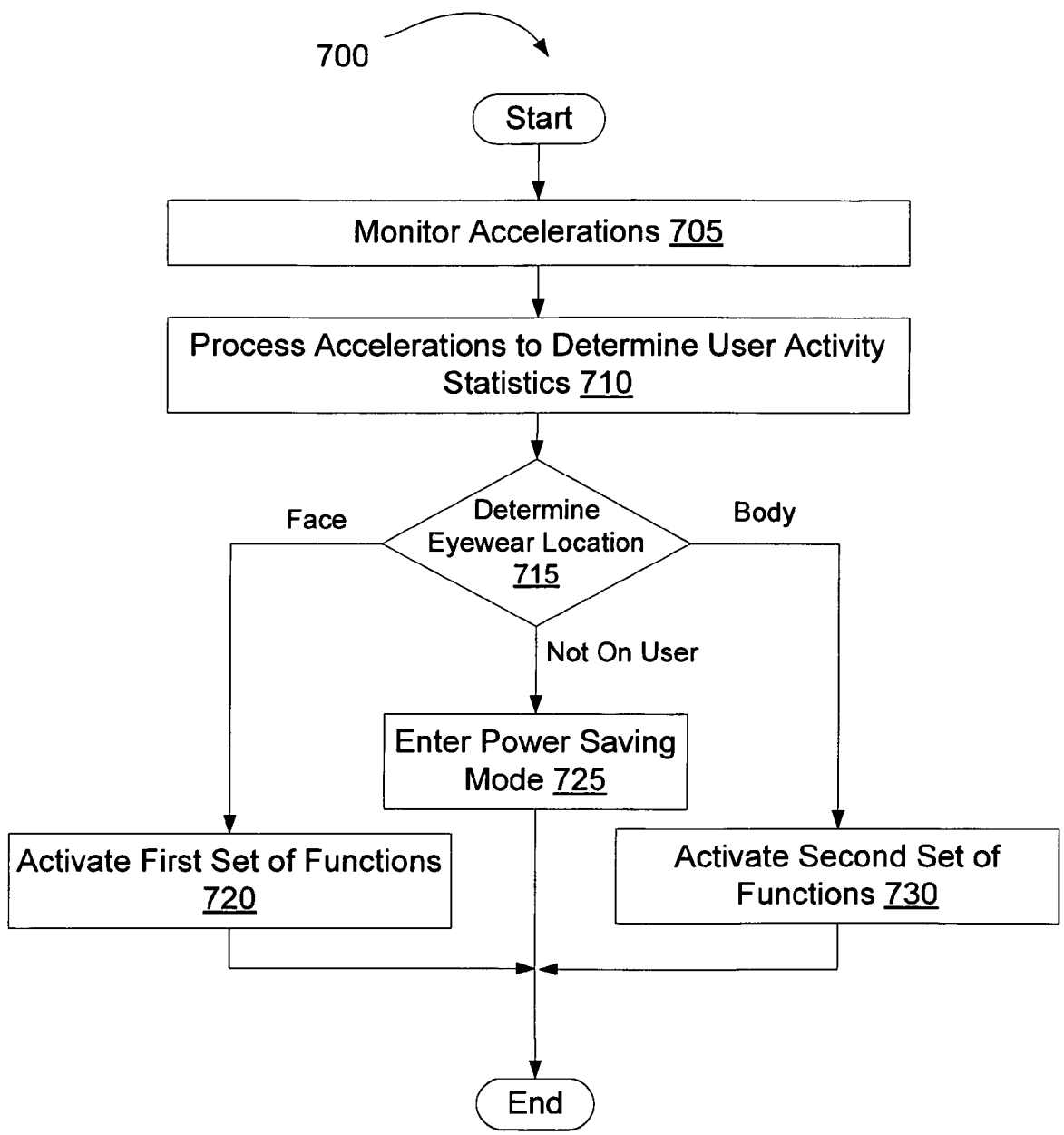
FIG. 7 illustrates a flow diagram for a method of monitoring human activity using an inertial sensor, in accordance with another of the present invention.

FIG. 7 illustrates a flow diagram for a method 700 of monitoring human activity using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 700 is performed by the electronic device 100 of FIG. 1. In one embodiment, method 700 is performed by the motion identification system 200 of FIG. 2.

Referring to FIG. 7, method 700 includes obtaining acceleration measurement data (block 705). Acceleration measurement data may be obtained from an inertial sensor, or other acceleration monitoring device. At block 710, the accelerations are processed to determine user activity statistics. In one embodiment, the accelerations are processed by a motion processor.

At block 715, the acceleration measurement data is analyzed to determine a location of the eyewear. In one embodiment, the process can determine whether the eyewear is disposed on a user's face, elsewhere on a user's body (e.g., in a pocket, backpack, in the user's hair, about a user's neck, etc.), or not disposed on a user's body. In one embodiment, an orientation of the eyewear is determined (e.g., by determining a dominant axis). This orientation can be used to determine if the eyewear is on the user's face. For example, if acceleration measurements are detected, and the eyewear is detected to have a first axis that is approximately aligned with gravity, it can be determined that the eyewear is disposed on a user's face. If the eyewear has any other orientation, it can be determined that the eyewear is disposed elsewhere on the user's body. If no accelerations are measured, it can be determined that the eyewear is not disposed on a person.

If the eyewear is determined to be disposed on the user's face, the method proceeds to block 720, and a first set of functions is activated. The first set of functions may include functions that can operate regardless of placement of the eyewear on the user, such as activity identification, counting of periodic human motions, etc. The first set of functions may also include functions that operate best when the eyewear is disposed approximately along a line of symmetry of the user, such as gait analysis, comparison between motions of the user's left and user's right, and so on.

If the eyewear is determined to be disposed elsewhere on the user's body, the method proceeds to block 730, and a second set of functions is activated. The second set of functions may include those functions that can operate regardless of placement of the eyewear on the user, but may not include those functions that operate best when the eyewear is disposed approximately along a line of symmetry of the user. If the eyewear is determined not to be disposed on the user, the method proceeds to block 725, and a power saving mode is activated. Under the power saving mode some or all functions may be disabled.

Figure 8:
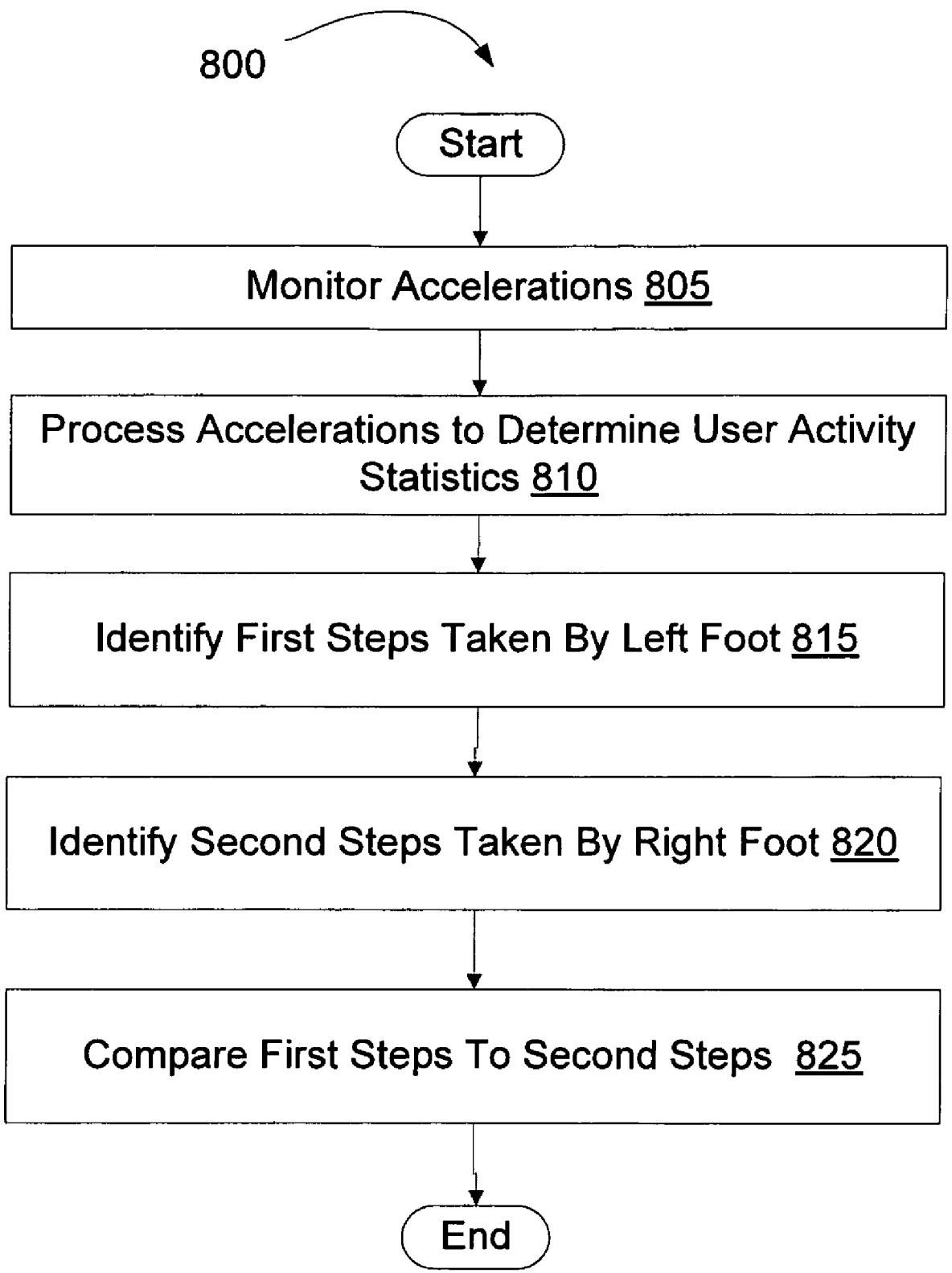
FIG. 8 illustrates a flow diagram for a method of monitoring human activity using an inertial sensor, in accordance with yet another embodiment of the present invention.

FIG. 8 illustrates a flow diagram for a method 800 of monitoring human activity using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 800 is performed by the electronic device 100 of FIG. 1. In a further embodiment, method 800 is performed if the electronic device 100 is located approximately at a line of symmetry of a user. In one embodiment, method 800 is performed by the motion identification system 200 of FIG. 2.

Referring to FIG. 8, method 800 includes obtaining acceleration measurement data (block 805). Acceleration measurement data may be obtained from an inertial sensor, or other acceleration monitoring device. At block 810, the accelerations are processed to determine user activity statistics. In one embodiment, the accelerations are processed by a motion processor.

At block 815, first steps taken by a left foot of a user are identified. At block 820, second steps taken by a right foot of the user are identified. At block 825, the first steps are compared to the second steps. Based on this comparison, the process can analyze characteristics of the user's gait. For example, the process can determine that a user's right leg is weaker than the user's left leg based on differences in forces exerted by the legs. The process can also determine, for example, that a user has too much spring in their step (e.g., that he/she is bouncing as they run), that a user's stride is too long or too short for his or her height (which can be entered by a user), etc. This data can be useful for training purposes and to prevent injury.

Figure 9:
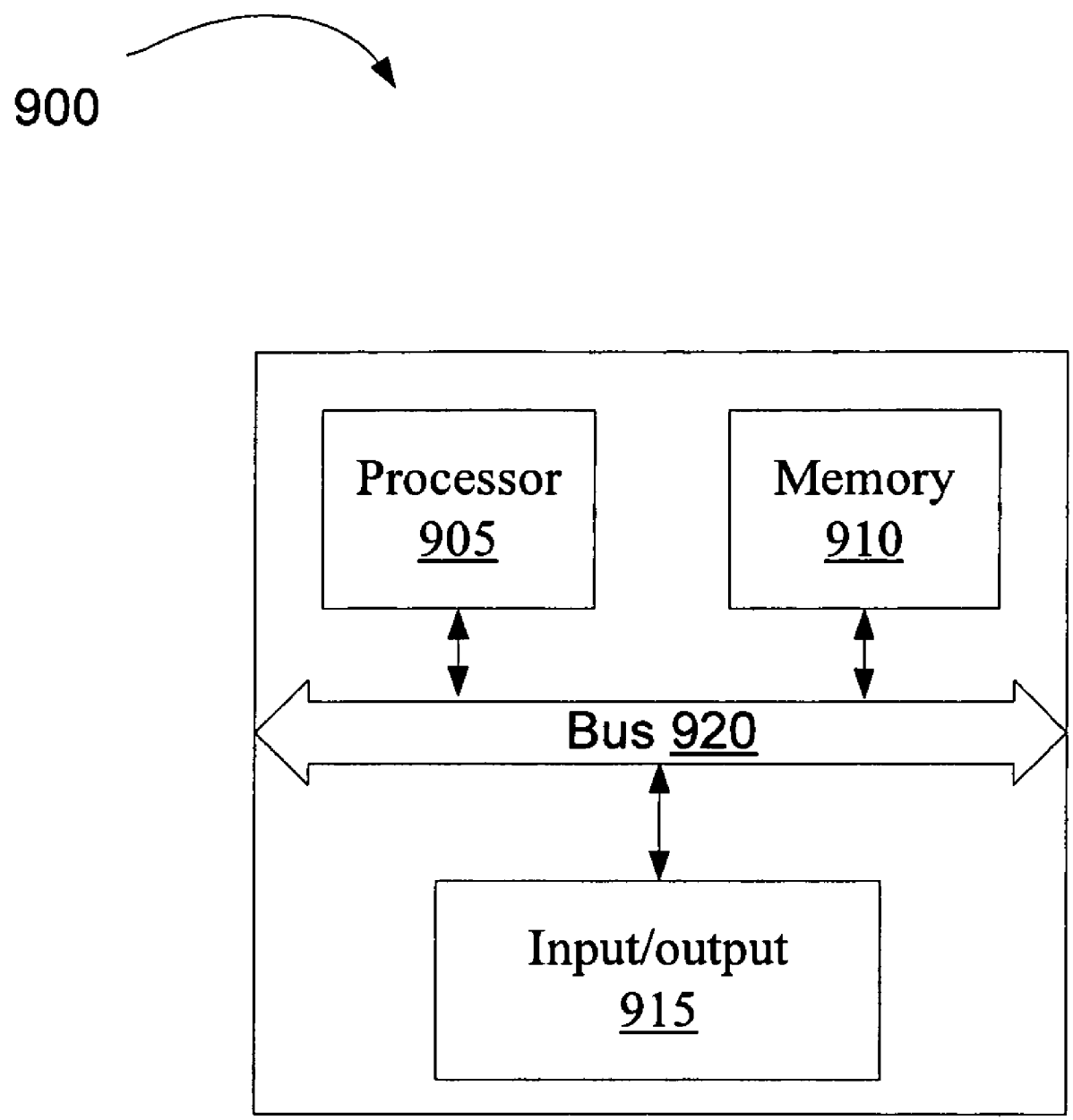
FIG. 9 illustrates a block diagram of a machine in the exemplary form of a computer system, in accordance with an embodiment of the present invention.

FIG. 9 illustrates a block diagram of a machine in the exemplary form of a computer system 900 within which a set of instructions, for causing the machine to perform any one or more of the methodologies discussed herein, may be executed. The exemplary computer system 900 includes a processing device (processor) 905, a memory 910 (e.g., read-only memory (ROM), a storage device, a static memory, etc.), and an input/output 915, which communicate with each other via a bus 920. Embodiments of the present invention may be performed by the computer system 900, and/or by additional hardware components (not shown), or may be embodied in machine-executable instructions, which may be used to cause processor 905, when programmed with the instructions, to perform the method described above. Alternatively, the method may be performed by a combination of hardware and software.

Processor 905 represents one or more general-purpose processing devices such as a microprocessor, central processing unit, or the like. More particularly, the processor 905 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 905 may also be one or more special-purpose processing devices such as an application specific integrated circuit (ASIC), a field programmable gate array (FPGA), a digital signal processor (DSP), network processor, or the like.

The present invention may be provided as a computer program product, or software, that may be stored in memory 910. Memory 910 may include a machine-readable medium having stored thereon instructions, which may be used to program exemplary computer system 900 (or other electronic devices) to perform a process according to the present invention. Other machine-readable mediums which may have instruction stored thereon to program exemplary computer system 900 (or other electronic devices) include, but are not limited to, floppy diskettes, optical disks, CD-ROMS, and magneto-optical disks, ROMS, RAMs, EPROMS, EEPROMS, magnetic or optical cards, flash memory, or other type of media or machine-readable mediums suitable for storing electronic instructions.

Input/output 915 may provide communication with additional devices and/or components. Thereby, input/output 915 may transmit data to and receive data from, for example, networked computers, servers, mobile devices, etc.

In the foregoing description, numerous specific details have been set forth such as examples of specific systems, languages, components, etc. in order to provide a thorough understanding of the present invention. It will be apparent, however, to one skilled in the art that these specific details need not be employed to practice the present invention. In other instances, well known materials or methods have not been described in detail in order to avoid unnecessarily obscuring the present invention.

In the foregoing specification, the invention has been described with reference to specific exemplary embodiments thereof. It will, however, be evident that various modifications and changes may be made thereto without departing from the broader scope of the invention as set forth in the appended claims. The specification and drawings are, accordingly, to be regarded in an illustrative rather than a restrictive sense.

What is claimed is:

1. A method of monitoring user activity using an inertial sensor, comprising:
    obtaining, by a processor, acceleration measurement data from an inertial sensor disposed in eyewear; and
    processing the acceleration measurement data by the processor to determine an identification of a current user activity from a plurality of user activities that are determinable by the processor based on the acceleration measurement data, the processing comprising:
        comparing the acceleration measurement data to a plurality of motion criteria sets, each of the motion criteria sets distinguishing a distinct activity of the plurality of user activities;
        determining that the acceleration measurement data satisfies motion criteria in a particular motion criteria set based on the comparison; and
        identifying a particular user activity associated with the particular motion criteria set as the current user activity.

2. The method of claim 1, further comprising:
    determining a user activity statistic associated with the identified user activity;
    formatting the user activity statistic to a generic format readable by a plurality of devices; and
    transmitting the formatted user activity statistic.

3. The method of claim 1, further comprising:
    determining a user activity statistic associated with the identified user activity;
    monitoring a metric from an additional sensor; and
    correlating the metric to the user activity statistic.

4. The method of claim 3, further comprising:
    using the correlation of the metric to the user activity statistic to increase accuracy of the user activity statistic.

5. The method of claim 1, further comprising:
    determining a user activity statistic associated with the identified user activity; and
    providing user feedback based the user activity statistic, the user feedback including at least one of aural, visual and tactile feedback.

6. The method of claim 5, wherein the user feedback includes at least one of an indication to speed up performance of the user activity and an indication to slow down the performance of the user activity.

7. The method of claim 5, wherein the visual feedback includes a display on a lens of the eyewear, the display being viewable to a user wearing the eyewear.

8. The method of claim 1, further comprising:
    receiving user input to display a requested user activity statistic associated with the identified user activity, the user input being received by at least one of a control mounted on the eyewear, a speech command, an external remote control wirelessly connected to the eyewear, and a motion command interface; and
    displaying the requested user activity statistic.

9. The method of claim 1, further comprising:
    determining whether the eyewear is disposed on a user's face, is otherwise disposed on the user, or is not disposed on the user.

10. The method of claim 9, further comprising:
    activating a first set of functions if the eyewear is disposed on the user's face; and
    activating a second set of functions if the eyewear is disposed elsewhere on the user.

11. The method of claim 1 wherein the eyewear is disposed on a user's face such that the eyewear is approximately aligned with an axis of symmetry of the user, the method further comprising:
    identifying first accelerations caused by motions from a right half of the user's body; and
    identifying second accelerations caused by motions from a left half of the user's body.

12. The method of claim 11, further comprising:
    identifying first steps taken by a left foot of the user;
    identifying second steps taken by a right foot of the user; and
    comparing acceleration measurements of the first steps to acceleration measurements of the second steps.

13. A non-transitory machine-accessible medium including instructions that, when executed by a machine, cause the machine to perform a method comprising:
    obtaining acceleration measurement data from an inertial sensor disposed in eyewear; and
    processing the acceleration measurement data to determine an identification of a current user activity from a plurality of determinable user activities, the processing comprising:
        comparing the acceleration measurement data to a plurality of motion criteria sets, each of the motion criteria sets distinguishing a distinct activity of the plurality of user activities;
        determining that the acceleration measurement data satisfies motion criteria in a particular motion criteria set that distinguishes a particular user activity based on the comparison; and
        identifying the particular user activity associated with the particular motion criteria set as the current user activity.

14. The non-transitory machine-accessible medium of claim 13, the method further comprising:
    determining a user activity statistic associated with the identified user activity;
    formatting the user activity statistic to a generic format readable by a plurality of devices; and
    transmitting the formatted user activity statistic.

15. The non-transitory machine-accessible medium of claim 13, further comprising:
    determining a user activity statistic associated with the identified user activity;
    monitoring a metric from an additional sensor; and
    correlating the metric to the user activity statistic.

16. The non-transitory machine-accessible medium of claim 13, the method further comprising:
    determining a user activity statistic associated with the identified user activity; and
    providing user feedback based the user activity statistic, the user feedback including at least one of aural, visual and tactile feedback.

17. The non-transitory machine-accessible medium of claim 16, wherein the visual feedback includes a display on a lens of the eyewear, the display being viewable to a user wearing the eyewear.

18. The non-transitory machine-accessible medium of claim 13, the method further comprising:
   receiving user input to display a requested user activity statistic associated with the identified user activity, the user input being received by at least one of a control mounted on the eyewear, a speech command, an external remote control wirelessly connected to the eyewear, and a motion command interface; and
   displaying the requested user activity statistic.

19. An inertial sensor based device, comprising:
   eyewear;
   an inertial sensor disposed in the eyewear to monitor accelerations; and
   a processor disposed in the eyewear and coupled to the inertial sensor to receive acceleration measurement data from the inertial sensor, and to process the acceleration measurement data to determine a current user activity from among a plurality of device determinable user activities, the processing comprising:
      comparing the acceleration measurement data to first motion criteria that distinguishes a first user activity and second motion criteria that distinguishes a second user activity; and
      identifying the first user activity as the current user activity based on the comparison.

20. The inertial sensor based device of claim 19, further comprising:
   the processor to determine a user activity statistic associated with the identified user activity; and
   a transmitter to transmit the user activity statistic, wherein the user activity statistic is formatted to a generic format readable by a plurality of devices prior to transmission.

21. The inertial sensor based device of claim 19, further comprising:
   the processor to determine a user activity statistic associated with the identified user activity; and
   a memory to store at least one of the acceleration measurement data and the user activity statistic.

22. The inertial sensor based device of claim 19, further comprising:
   a feedback element to provide at least one of aural, visual and tactile feedback.

23. The inertial sensor based device of claim 22, wherein the feedback element is a display on a lens of the eyewear, the display being viewable to a user wearing the eyewear.

24. The inertial sensor based device of claim 19, further comprising:
   the processor to determine a user activity statistic associated with the identified user activity; and
   an additional sensor to provide a metric to correlate to the user activity statistic.

25. The inertial sensor based device of claim 19, further comprising:
   an input to receive user input, the input including least one of a control mounted on the eyewear, a speech command module, and a motion command interface module.

26. The inertial sensor based device of claim 19, further comprising:
   a remote control wirelessly connected to the inertial sensor based device.

\* \* \* \* \*